United States Patent
Minter et al.

(10) Patent No.: US 8,022,167 B2
(45) Date of Patent: Sep. 20, 2011

(54) PROCESS FOR THE SYNTHESIS OF DIAMINOPYRIDINES FROM GLUTARONITRILES

(76) Inventors: Aaron Minter, Wilmington, DE (US); Berlin Stokes, Newark, DE (US)

(*) Notice: Subject to any disclaimer, the term of this patent is extended or adjusted under 35 U.S.C. 154(b) by 0 days.

(21) Appl. No.: 12/519,592

(22) PCT Filed: Dec. 18, 2007

(86) PCT No.: PCT/US2007/025816
§ 371 (c)(1),
(2), (4) Date: Jun. 17, 2009

(87) PCT Pub. No.: WO2008/082509
PCT Pub. Date: Jul. 10, 2008

(65) Prior Publication Data
US 2010/0029948 A1 Feb. 4, 2010

Related U.S. Application Data

(60) Provisional application No. 60/876,577, filed on Dec. 21, 2006.

(51) Int. Cl.
*C08G 63/06* (2006.01)
*C08G 63/02* (2006.01)

(52) U.S. Cl. .......... 528/208; 544/82; 546/250; 528/176; 528/190; 528/198

(58) Field of Classification Search .................... 544/82; 546/250; 528/176, 190, 198, 208
See application file for complete search history.

(56) References Cited

U.S. PATENT DOCUMENTS

| | | | |
|---|---|---|---|
| 2,816,879 A | 12/1957 | Wittbecker | |
| 3,554,966 A | 1/1971 | Jones et al. | |
| 4,051,140 A | 9/1977 | Gelbein et al. | |
| 4,086,237 A * | 4/1978 | Daum et al. | 546/252 |
| 4,110,412 A | 8/1978 | Danzig et al. | |
| 4,153,783 A | 5/1979 | Gagliani et al. | |
| 4,451,642 A | 5/1984 | Frazer et al. | |
| 4,603,207 A | 7/1986 | DiCosimo et al. | |
| 4,736,015 A | 4/1988 | Rabilloud et al. | |
| 4,737,571 A | 4/1988 | Hodge et al. | |
| 4,876,348 A | 10/1989 | DiCosimo et al. | |
| 5,028,713 A | 7/1991 | DiCosimo et al. | |
| 5,061,784 A | 10/1991 | Mueller et al. | |
| 5,066,809 A | 11/1991 | Suresh et al. | |
| 5,674,969 A | 10/1997 | Sikkema et al. | |
| 5,693,227 A | 12/1997 | Costa | |
| 5,939,553 A * | 8/1999 | Reichwein et al. | 546/250 |
| 6,118,003 A | 9/2000 | McAteer et al. | |
| 6,569,987 B1 | 5/2003 | Ohba et al. | |

FOREIGN PATENT DOCUMENTS

| | | |
|---|---|---|
| CA | 2355316 | 6/2010 |
| EP | 0062264 A | 10/1982 |
| EP | 0478144 A | 4/1992 |
| EP | 0825985 A | 3/1998 |
| WO | 9425506 A1 | 11/1994 |
| WO | 2006104974 A1 | 10/2006 |

OTHER PUBLICATIONS

Takata et al. "Synthesis of Methylpyridine and 1,8-Naphthylidine derivatives" Bulletin of the Chemical Society of Japan vol. 35 col. 9, 1962, 1438-1443.*
International Search Report, PCT/US2007/025816, Dated Jul. 17, 2009.
Advanced Inorganic Chemistry by Cotton and Wilkinson, Interscience New York, 2nd Edition 1966 (Book Not Included).
Millich and Carraher, Interfacial Syntheses, vol. 2, Dekker, New York, 1977 (Book Not Included).
Kumar et al., Chelating Copolymers Containing Photosensitive Functionalities, Macromolecules, American Chemical Society, vol. 17, 1984, pp. 2463-2467.
Tinant et al., Captodative Substitution and Cyclopropane Geometry, Part 5.1 X-Ray Structure of Five New Compounds and Asymmetry Parameters of the Substituents, J. Chem. Soc., Perkin Trans. ii, 1988, pp. 1045-1052.

* cited by examiner

*Primary Examiner* — Terressa M Boykin

(57) ABSTRACT

A liquid-phase process is provided for the manufacture from glutaronitriles and related compounds of 2,6-diaminopyridine and related compounds, which are used industrially as compounds and as components in the synthesis of a variety of useful materials. The synthesis proceeds by means of a dehydrogenative aromatization process.

19 Claims, No Drawings

PROCESS FOR THE SYNTHESIS OF DIAMINOPYRIDINES FROM GLUTARONITRILES

This application claims the benefit of U.S. Provisional Application No. 60/876,577, filed 21 Dec. 2006, which is incorporated in its entirety as a part hereof for all purposes.

TECHNICAL FIELD

This invention relates to the manufacture of 2,6-diaminopyridine and related compounds, which are used industrially as compounds and as components in the synthesis of a variety of useful materials.

BACKGROUND

The compound 2,6-diaminopyridine ("DAP"), which is shown by the structural formula below

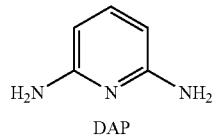

DAP is a useful starting material for preparing monomers for rigid rod polymers such as described in WO 94/25506, as well as for dyes, metal ligands, medicines and pesticides.

It is well-known to prepare DAP by means of the Chichibabin amination reaction in which pyridine is reacted with sodium amide in an organic solvent. This is a complicated reaction requiring relatively severe conditions (e.g. 200° C. at elevated pressure). Additionally, handling sodium amide and isolating the desired product from this complex mixture are difficult operations to perform on a commercial scale.

Pyridine derivatives have also been synthesized through the conversion of acylic dinitriles (see, for example, GB 2,165,844; and U.S. Pat. Nos. 5,066,809; 4,876,348; 6,118,003; 4,603,207; 5,028,713; and 4,051,140). There are several examples of this type of transformation in the vapor phase and, to a lesser extent, in the liquid phase. For example, U.S. Pat. No. 4,876,348 teaches the ammoxidation of 2-methylglutaronitrile to 3-cyanopyridine. The two-step process involves the conversion of 2-methylglutaronitrile to a mixture of 3-methylpyridine and 3-methylpiperidine, followed by the vapor phase ammoxidation of this mixture with $NH_3$ and $O_2$ in the presence of a complex metal oxide to give the product 3-cyanopyridine.

A need thus remains for a process wherein, on an industrial scale, it would be possible to form pyridine derivatives in the liquid phase in the presence of a heterogeneous catalyst, which would facilitate separating and recycling the catalyst.

SUMMARY

The inventions disclosed herein include processes for the preparation of diaminopyridines and related compounds, processes for the preparation of products into which diaminopyridines and related compounds can be converted, and the products obtained and obtainable by such processes.

One embodiment of this invention involves a process for the synthesis of a compound as described by the structure of Formula (I)

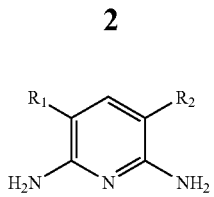

by contacting a compound as described by the structure of Formula (II)

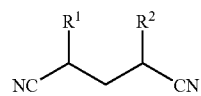

with a chemical oxidant and/or a dehydrogenation catalyst in liquid ammonia neat, or in a mixture of liquid ammonia and a polar, aprotic solvent, to form a reaction mixture; and heating the reaction mixture to produce a Formula (I) compound; wherein $R^1$ and $R^2$ are each independently selected from (a) H; (b) a hydrocarbyl group; (c) $NR^3R^4$ wherein $R^3$ and $R^4$ are each independently selected from H and a hydrocarbyl group;

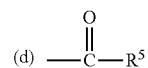

wherein $R^5$ is a hydrocarbyl group; and (e) $YR^6$ wherein Y is selected from O and S and $R^6$ is selected from H, a hydrocarbyl group, and

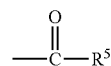

wherein $R^5$ is a hydrocarbyl group.

A further embodiment of the processes hereof involves a process for preparing a Formula (I) compound that further includes a step of subjecting the Formula (I) compound to a reaction (including a multi-step reaction) to prepare therefrom a compound, monomer, oligomer or polymer.

In yet another embodiment of this invention, a new compound as described by the structure of Formula (III) is provided:

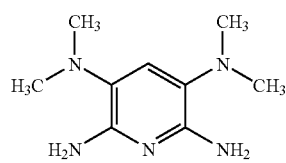

DETAILED DESCRIPTION

In a process as described herein, compounds of Formula (I) are prepared from glutaronitrile and related compounds by means of a dehydrogenative aromatization process in the presence of a chemical oxidant and/or a dehydrogenation catalyst.

In one embodiment of the processes hereof, a compound of Formula (I) is synthesized from an acylic dinitrile compound of Formula (II) by contacting the acylic dinitrile compound with a chemical oxidant and/or a dehydrogenation catalyst in liquid ammonia neat or in a mixture of ammonia and a polar, aprotic solvent to form a reaction mixture, and heating the reaction mixture to produce the Formula (I) product.

In Formulas (I) and (II), $R^1$ and $R^2$ are each independently selected from (a) H; (b) a hydrocarbyl group; (c) $NR^3R^4$ wherein $R^3$ and $R^4$ are each independently selected from H and a hydrocarbyl group;

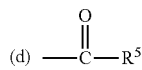

wherein $R^5$ is a hydrocarbyl group; and (e) $YR^6$ wherein Y is selected from O and S and $R^6$ is selected from H, a hydrocarbyl group, and

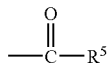

wherein $R^5$ is a hydrocarbyl group.

Examples of hydrocarbyl groups suitable for use in $R^2$ to $R^5$ include without limitation a $C_1$~$C_{18}$, or $C_1$~$C_{10}$, straight-chain or branched, saturated or unsaturated, substituted or unsubstituted, hydrocarbyl radical;

a $C_3$~$C_{12}$ cyclic aliphatic, saturated or unsaturated, substituted or unsubstituted, hydrocarbyl radical; or a $C_6$~$C_{12}$ aromatic substituted or unsubstituted hydrocarbyl radical.

In various embodiments, any one or more of $R^2$ to $R^5$ may be a methyl, ethyl, propyl, butyl, pentyl, hexyl or phenyl radical. In a substituted hydrocarbyl radical, one or more O or S atoms may optionally be substituted for any one or more of the in-chain or in-ring carbon atoms, provided that the resulting structure contains no —O—O— or —S—S— moieties, and provided that no carbon atom is bonded to more than one heteroatom.

Preferably, one or both of $R^1$ and $R^2$ is H. When $R^1$ and $R^2$ are both H, the acylic dinitrile is glutaronitrile ("GN") and the compound of Formula (I) is 2,6-diaminopyridine ("DAP"), as shown below:

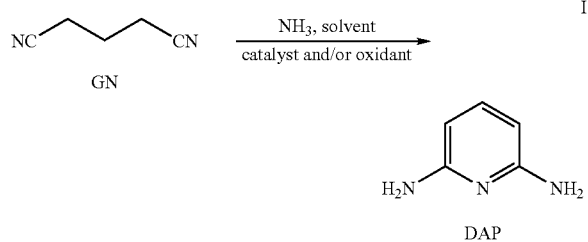

One or both of $R^1$ and $R^2$ may be $NH_2$. When $R^1$ and $R^2$ are both $NH_2$, the compound of Formula (II) is 2,4-diaminopentanedinitrile, and the compound of Formula (I) is 2,3,5,6-tetraminopyridine ("TAP") which itself is a useful industrial intermediate.

When the compound of Formula (II) is 2,4-bis(dimethylamino)pentanedinitrile [i.e. $R^1$ and $R^2$ are both $N(CH_3)_2$], a new compound $N^3,N^3,N^5,N^5$-tetramethylpyridine-2,3,5,6-tetraamine, as shown by the structure of Formula (III), is produced:

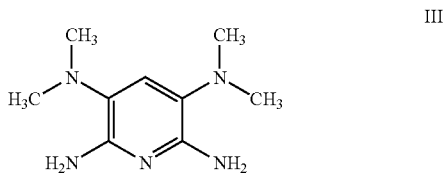

Various compounds of Formula (II), as used in the processes hereof, may be synthesized by processes known in the art, or are available commercially from suppliers such as Alfa Aesar (Ward Hill, Mass.), City Chemical (West Haven, Conn.), Fisher Scientific (Fairlawn, N.J.), Sigma-Aldrich (St. Louis, Mo.) or Stanford Materials (Aliso Viejo, Calif.).

In a process hereof, a compound of Formula (II) is contacted with a chemical oxidant and/or a dehydrogenation catalyst. Thus, a chemical oxidant and a dehydrogenation catalyst may each be used with or without (i.e. in the absence of) the other.

Chemical oxidants suitable for use herein include without limitation sulfur, sulfur dioxide, oxygen, selenium, 2,3-dichloro-5,6-dicyano-p-benzoquinone ("DDQ"), 2,3,5,6-tetrachloro-p-benzoquinone ("chloranil"), aluminum chloride, arsenic oxide, manganese dioxide, potassium ferricyanide, nitrobenzene, chlorine, bromine, iodine, and the like.

A dehydrogenation catalyst as used herein may be a homogeneous catalyst or a heterogeneous catalyst. A dehydrogenation catalyst suitable for use herein typically contains at least one metal or metal salt wherein the metal or metal salt is selected, for example, from elements of Groups IVA, VA, VIA, VIIA, VIII, IB, and IIB, and salts of said elements [as such groups are described in the periodic table in a reference such as *Advanced Inorganic Chemistry* by Cotton and Wilkinson, Interscience New York, 2nd Ed. (1966)]. A particular metal or metal salt may be selected from Group VIII elements and salts of said elements (e.g. iron, cobalt and nickel), and/or the platinum group metals including ruthenium, rhodium, palladium, osmium, iridium and platinum. The platinum group metals and their salts are preferred, more preferably platinum and palladium and their salts. Sponge metal catalysts may also be effective, including without limitation Raney iron, Raney nickel and Raney cobalt. Raney nickel is preferred.

In a heterogeneous catalyst, a metal or metal salt may be deposited upon any suitable support with a sufficiently high surface area. The support may be amorphous or may possess a crystalline structure or contain both amorphous and crystalline portions. The support may be a solid metal oxide or solid non-metal oxide, each with surface —OH groups. Examples of such metal oxides are those from tri- and tetravalent metals, which may be a transition or non-transition metal or any rare earth such as alumina, titania, cobaltic oxide, zirconia, ceria, molybdenum oxide and tungsten oxide. An example of a typical non-metal oxide is silica. The support may also be a zeolite or zeotype material having a structure made up of tetrahedra joined together through oxygen atoms to produce an extended network with channels of molecular dimensions. The zeolite/zeotype materials have SiOH and/or AlOH groups on the external or internal surfaces. The support may also be activated carbon, coke or charcoal. Preferably, the support is at least one of alumina, silica, silicalite, ceria, titania, or carbon, more preferably alumina, silica or carbon.

The liquid ammonia, whether used neat or in a solvent, is typically used in an amount of from about 1 to about 100 moles per mole of compound of Formula (II). When a polar, aprotic solvent is used, examples of suitable solvents include without limitation 1,4-dioxane, tetrahydrofuran, acetone, acetonitrile, dimethylformamide, and pyridine. Mixed solvents can be used, such as 1,4-dioxane plus pyridine, but using ammonia neat is preferred (the term "neat" referring to the absence of solvent).

The reaction may be run at a temperature that is typically in the range of about 200° C. to about 300° C. Reaction time is typically about 3 to about 45 hours. The reaction is preferably run in a closed vessel.

A compound of Formula (I) or (III) (a "Pyridine Product") may, as desired, be isolated and recovered. The Pyridine Product may also, however, be subjected with or without recovery from the reaction mixture to further steps to convert it to another product such as another compound (e.g. a monomer), or an oligomer or a polymer. Another embodiment of a process hereof thus provides a process for converting a Pyridine Product, through a reaction (including a multi-step reaction), into another compound, or into an oligomer or a polymer. A Pyridine Product may be made by a process such as described above, and then converted, for example, by being subjected to a polymerization reaction to prepare an oligomer or polymer therefrom, such as those having amide functionality, imide functionality, or urea functionality, or a pyridobisimidazole-2,6-diyl(2,5-dihydroxy-p-phenylene) polymer.

A Pyridine Product such as a diaminopyridine may be converted into a polyamide oligomer or polymer by reaction with a diacid (or diacid halide) in a process in which, for example, the polymerization takes place in solution in an organic compound that is liquid under the conditions of the reaction, is a solvent for both the diacid(halide) and the diaminopyridine, and has a swelling or partial salvation action on the polymeric product. The reaction may be effected at moderate temperatures, e.g. under 100° C., and is preferably effected in the presence of an acid acceptor that is also soluble in the chosen solvent. Suitable solvents include methyl ethyl ketone, acetonitrile, N,N-dimethylacetamide dimethyl formamide containing 5% lithium chloride, and N-methylpyrrolidone containing a quaternary ammonium chloride such as methyl tri-n-butyl ammonium chloride or methyl-tri-n-propyl ammonium chloride. Combination of the reactant components causes generation of considerable heat and the agitation, also, results in generation of heat energy. For that reason, the solvent system and other materials are cooled at all times during the process when cooling is necessary to maintain the desired temperature. Processes similar to the foregoing are described in U.S. Pat. Nos. 3,554,966; 4,737,571; and CA 2,355,316.

A Pyridine Product such as a diaminopyridine may also be converted into a polyamide oligomer or polymer by reaction with a diacid (or diacid halide) in a process in which, for example, a solution of the diaminopyridine in a solvent may be contacted in the presence of an acid acceptor with a solution of a diacid or diacid halide, such as a diacid chloride, in a second solvent that is immiscible with the first to effect polymerization at the interface of the two phases. The diaminopyridine may, for example, be dissolved or dispersed in a water containing base with the base being used in sufficient quantities to neutralize the acid generated during polymerization. Sodium hydroxide may be used as the acid acceptor. Preferred solvents for the diacid(halide) are tetrachloroethylene, methylenechloride, naphtha and chloroform. The solvent for the diacid(halide) should be a relative non-solvent for the amide reaction product, and be relatively immiscible in the amine solvent. A preferred threshold of immiscibility is as follows: an organic solvent should be soluble in the amine solvent not more than between 0.01 weight percent and 1.0 weight percent. The diaminopyridine, base and water are added together and vigorously stirred. High shearing action of the stirrer is important. The solution of acid chloride is added to the aqueous slurry. Contacting is generally carried out at from 0° C. to 60° C., for example, for from about 1 second to 10 minutes, and preferably from 5 seconds to 5 minutes at room temperature. Polymerization occurs rapidly. Processes similar to the foregoing are described in U.S. Pats. No. 3,554,966 and 5,693,227.

A Pyridine Product such as a diaminopyridine may also be converted into a polyimide oligomer or polymer by reaction with a tetraacid (or halide derivative thereof) or a dianhydride in a process in which each reagent (typically in equimolar amounts) is dissolved in a common solvent, and the mixture is heated to a temperature in the range of 100~250° C. until the product has a viscosity in the range of 0.1~2 dL/g. Suitable acids or anhydrides include benzhydrol 3,3',4,4'-tetracarboxylic acid, 1,4-bis(2,3-dicarboxyphenoxy)benzene dianhydride, and 3,3',4,4'-benzophenone tetracarboxylic acid dianhydride. Suitable solvents include cresol, xylenol, diethyleneglycol diether, gamma-butyrolactone and tetramethylenesulfone. Alternatively, a polyamide-acid product may be recovered from the reaction mixture and advanced to a polyimide by heating with a dehydrating agent such as a mixture of acetic anhydride and beta picoline. Processes similar to the foregoing are described in U.S. Pats. No. 4,153,783; 4,736,015; and 5,061,784.

A Pyridine Product such as a diaminopyridine may also be converted into a polyurea oligomer or polymer by reaction with a polyisocyanate, representative examples of which include toluene diisocyanate; methylene bis(phenyl isocyanates); hexamethylene diisocycanates; phenylene diisocyanates. The reaction may be run in solution, such as by dissolving both reagents in a mixture of tetramethylene sulfone and chloroform with vigorous stirring at ambient temperature. The product can be worked up by separation with water, or acetone and water, and then dried in a vacuum oven. Processes similar to the foregoing are described in U.S. Pat. No. 4,451,642 and Kumar, Macromolecules 17, 2463 (1984). The polyurea forming reaction may also be run under interfacial conditions, such as by dissolving the diaminopyridine in an aqueous liquid, usually with an acid acceptor or a buffer. The polyisocyanate is dissolved in an organic liquid such as benzene, toluene or cyclohexane. The polymer product forms at the interface of the two phases upon vigourous stirring. Processes similar to the foregoing are described in U.S. Pat. No. 4,110,412 and Millich and Carraher, Interfacial Syntheses, Vol. 2, Dekker, New York, 1977. A diaminopyridine may also be converted into a polyurea by reaction with phosgene, such as in an interfacial process as described in U.S. Pat. No. 2,816,879.

A Pyridine Product such as a tetramino pyridine may be converted to a pyridobisimidazole-2,6-diyl(2,5-dihydroxy-p-phenylene) polymer by polymerizing a 2,5-dihydroxyterephthalic acid with the trihydrochloride-monohydrate of tetraminopyridine in strong polyphosphoric acid under slow heating above 100° C. up to about 180° C. under reduced pressure, followed by precipitation in water, as disclosed in U.S. Pat. No. 5,674,969 (which is incorporated in its entirety as a part hereof for all purposes); or by mixing the monomers at a temperature from about 50° C. to about 110° C., and then 145° C. to form an oligomer, and then reacting the oligomer at a temperature of about 160° C. to about 250° C. as disclosed in U.S. Provisional Application No. 60/665,737, filed Mar. 28, 2005 (which is incorporated in its entirety as a part hereof for all purposes), published as WO 2006/104974. The pyridobisimidazole-2,6-diyl(2,5-dihydroxy-p-phenylene) polymer so produced may be, for example, a poly(1,4-(2,5-dihydroxy)phenylene-2,6-pyrido[2,3-d: 5,6-d']bisimidazole) polymer, or a poly[(1,4-dihydrodiimidazo[4,5-b:4',5'-e]pyridine-2,6-diyl) (2,5-dihydroxy-1,4-phenylene)]polymer. The pyridobisimidazole portion thereof may, however, be replaced by any or more of a benzobisimidazole, benzobisthiazole, benzobisoxazole, pyridobisthiazole and a pyridobisoxazole; and the 2,5-dihydroxy-p-phenylene portion thereof may be replaced by the derivative of one or more of isophthalic acid, terephthalic acid, 2,5-pyridine dicarboxylic acid, 2,6-naphthalene dicarboxylic acid, 4,4'-diphenyl dicarboxylic acid, 2,6-quinoline dicarboxylic acid, and 2,6-bis(4-carboxyphenyl)pyridobisimidazole.

EXAMPLES

The advantageous attributes and effects of the processes hereof may be seen in a series of examples (Examples 1~11), as described below. The embodiments of these processes on which the examples are based are illustrative only, and the selection of those embodiments to illustrate the invention does not indicate that conditions, arrangements, approaches, steps, techniques, configurations or reactants not described in these examples are not suitable for practicing these processes, or that subject matter not described in these examples is excluded from the scope of the appended claims and equivalents thereof.

Materials.

The following materials were used in the examples. All commercial reagents, such as glutaronitrile (99%) and 2-methylglutaronitrile (99%), were obtained from Aldrich and used as received unless otherwise noted. Palladium (10 weight percent on activated carbon) or platinum (5 weight percent on activated carbon) slurry catalysts were obtained from Aldrich and used for all experiments unless otherwise noted. Anhydrous ammonia (99.99%) was obtained from Messer (GTS) and 2,4-bis(dimethylamino)pentanedinitrile was prepared according to procedures reported by Meerssche et al, *J. Chem. Soc. Perkin Trans. II*, 1988, 1045-52.

Methods

The conversion and selectivity of this reaction are influenced by the catalyst and conditions used. As used herein, the term "selectivity" for a product P denotes the molar fraction or molar percentage of P in the final product mix. As used herein, the term "conversion" denotes to how much reactant was used up as a fraction or percentage of the theoretical amount. The conversion times the selectivity thus equals the maximum "yield" of P; the actual yield, also referred to as "net yield," will normally be somewhat less than this because of sample losses incurred in the course of activities such as isolating, handling, drying, and the like. As used herein, the term "purity" denotes what percentage of the in-hand, isolated sample is actually the specified substance.

$^1$H and $^{13}$C NMR spectra were recorded at 500 and 100 MHz (CCAS), respectively, unless otherwise specified. Percent conversion, based on the mole fraction of reacted glutaronitrile (GN), and yield, based on the mole fraction of 2,6-diaminopyridine (DAP) or 2,6-diamino-3-methylpyridine (DAMP) produced in the reaction, were determined by $^1$H NMR spectral integration and/or gas chromatography (HP5890 Series II equipped with FID detector) using internal standards [2,6-Di-tert-butyl-4-methylphenol (BHT) and triethyleneglycoldiethylether (EEE), respectively] unless otherwise specified.

The meaning of abbreviations is as follows: "DAP" means 2,6-diaminopyridine, "eq." means equivalent "GN" means glutaronitrile, "h" means hour(s), "g" means gram(s), "mg" means milligrams, "mmol" means millimole(s), "MPa" means megapascal(s), "wt %" means weight percentage), "psi" means pounds per square inch, "MHz" means megahertz, "NMR" means nuclear magnetic resonance spectroscopy, "Pd.C" means palladium on carbon catalyst, "Pt.C" means platinum on carbon catalyst and "GC/MS" means gas chromatography/mass spectrometry.

Examples 1 through 9 demonstrate the preparation of 2,6-diaminopyridine by means of the reaction:

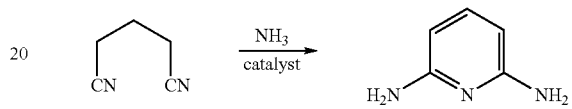

In Examples 1, 2, 3 and 4, the concentration of NH$_3$ is varied. In Examples 5, 6 and 7, the amount of catalyst is varied. In Example 8, different amounts of both catalyst and NH$_3$ are used. In Example 9, a Pt catalyst is used instead of Pd.

Example 1

Glutaronitrile (3.0 g, 31.9 mmol, 1 eq.) was combined with Pd.C (3.39 g, 3.19 mmol, 10 mol % of 10 wt % Pd on carbon) in a 400 mL Hastelloy shaker autoclave to which liquid NH$_3$ (1.0 g, 58.7 mmol, 1.8 eq.) was added. The mixture was heated at 200° C. for 45 h and maintained a reaction pressure of approximately 90 psi (0.62 MPa). The mixture was cooled to ambient temperature and the excess NH$_3$ removed by N$_2$ purge. The crude mixture was suspended in 200 mL anhydrous methanol, the catalyst was removed by gravity filtration, and the crude reaction mixture was concentrated in vacuo. Glutaronitrile conversion was >95% to give 2.43 mmol of 2,6-diaminopyridine in 7.6% net yield.

Example 2

Glutaronitrile (3.0 g, 31.9 mmol, 1 eq.) was combined with Pd.C (3.39 g, 3.19 mmol, 10 mol % of 10 wt % Pd on carbon) in a 400 mL Hastelloy shaker autoclave to which liquid NH$_3$ (11.0 g, 0.65 mol, 20.2 eq.) was added. The mixture was heated at 200° C. for 45 h and maintained a reaction pressure of approximately 800 psi (5.5 MPa). The mixture was cooled to ambient temperature and the excess NH$_3$ removed by N$_2$ purge. The crude mixture was suspended in 200 mL anhydrous methanol, the catalyst was removed by gravity filtration, and the crude reaction mixture was concentrated in vacuo. Glutaronitrile conversion was >95% to give 2.07 mmol of 2,6-diaminopyridine in 6.5% net yield.

Example 3

Glutaronitrile (3.0 g, 31.9 mmol, 1 eq.) was combined with Pd.C (3.39 g, 3.19 mmol, 10 mol % of 10 wt % Pd on carbon) in a 400 mL Hastelloy shaker autoclave to which liquid NH$_3$ (33.0 g, 1.94 mol, 60.7 eq.) was added. The mixture was heated at 200° C. for 45 h and maintained a reaction pressure of approximately 1700 psi (11.7 MPa). The mixture was cooled to ambient temperature and the excess NH$_3$ removed by $N_2$ purge. The crude mixture was suspended in 200 mL anhydrous methanol, the catalyst was removed by gravity filtration, and the crude reaction mixture was concentrated in vacuo. Glutaronitrile conversion was >95% to give 5.51 mmol of 2,6-diaminopyridine in 17.3% yield.

Example 4

Glutaronitrile (3.0 g, 31.9 mmol, 1 eq.) was combined with Pd.C (3.39 g, 3.19 mmol, 10 mol % of 10 wt % Pd on carbon) in a 400 mL Hastelloy shaker autoclave to which liquid $NH_3$ (43.5 g, 2.55 mol, 80.1 eq.) was added. The mixture was heated at 200° C. for 45 h and maintained a reaction pressure of approximately 2100 psi (14.5 MPa). The mixture was cooled to ambient temperature and the excess $NH_3$ removed by $N_2$ purge. The crude mixture was suspended in 200 mL anhydrous methanol, the catalyst was removed by gravity filtration, and the crude reaction mixture was concentrated in vacuo. Glutaronitrile conversion was >95% to give 1.68 mmol of 2,6-diaminopyridine in 5.3% net yield.

Example 5

Glutaronitrile (3.0 g, 31.9 mmol, 1 eq.) was combined with Pd.C (0.34 g, 0.32 mmol, 1 mol % of 10 wt % Pd on carbon) in a 400 mL Hastelloy shaker autoclave to which liquid $NH_3$ (33.0 g, 1.94 mol, 60.7 eq.) was added. The mixture was heated at 200° C. for 45 h and maintained a reaction pressure of approximately 1800 psi (12.4 MPa). The mixture was cooled to ambient temperature and the excess $NH_3$ removed by $N_2$ purge. The crude mixture was suspended in 200 mL anhydrous methanol, the catalyst was removed by gravity filtration, and the crude reaction mixture was concentrated in vacuo. Glutaronitrile conversion was >95% to give 0.05 mmol of 2,6-diaminopyridine in 0.2% net yield.

Example 6

Glutaronitrile (3.0 g, 31.9 mmol, 1 eq.) was combined with Pd.C (1.70 g, 1.60 mmol, 5 mol % of 10 wt % Pd on carbon) in a 400 mL Hastelloy shaker autoclave to which liquid $NH_3$ (33.0 g, 1.94 mol, 60.7 eq.) was added. The mixture was heated at 200° C. for 45 h and maintained a reaction pressure of approximately 1800 psi (12.4 MPa). The mixture was cooled to ambient temperature and the excess $NH_3$ removed by $N_2$ purge. The crude mixture was suspended in 200 mL anhydrous methanol, the catalyst was removed by gravity filtration, and the crude reaction mixture was concentrated in vacuo. Glutaronitrile conversion was >95% to give 4.86 mmol of 2,6-diaminopyridine in 15.5% net yield.

Example 7

Glutaronitrile (3.0 g, 31.9 mmol, 1 eq.) was combined with Pd.C (6.79 g, 6.38 mmol, 20 mol % of 10 wt % Pd on carbon) in a 400 mL Hastelloy shaker autoclave to which liquid $NH_3$ (33.0 g, 1.94 mol, 60.7 eq.) was added. The mixture was heated at 200° C. for 45 h and maintained a reaction pressure of approximately 1800 psi (12.4 MPa). The mixture was cooled to ambient temperature and the excess $NH_3$ removed by $N_2$ purge. The crude mixture was suspended in 200 mL anhydrous methanol, the catalyst was removed by gravity filtration, and the crude reaction mixture was concentrated in vacuo. Glutaronitrile conversion was >95% to give 4.466 mmol of 2,6-diaminopyridine in 14.6% net yield.

Example 8

Glutaronitrile (3.0 g, 31.9 mmol, 1 eq.) was combined with Pd.C (6.79 g, 6.38 mmol, 20 mol % of 10 wt % Pd on carbon) in a 400 mL Hastelloy shaker autoclave to which liquid $NH_3$ (43.5 g, 2.55 mol, 80.1 eq.) was added. The mixture was heated at 200° C. for 45 h and maintained a reaction pressure of approximately 2200 psi (15.2 MPa). The mixture was cooled to ambient temperature and the excess $NH_3$ removed by $N_2$ purge. The crude mixture was suspended in 200 mL anhydrous methanol, the catalyst was removed by gravity filtration, and the crude reaction mixture was concentrated in vacuo. Glutaronitrile conversion was >95% to give 5.22 mmol of 2,6-diaminopyridine in 16.5% yield.

Example 9

Glutaronitrile (94 mg, 1.0 mmol, 1 eq.) was combined with Pt.C (390 mg, 0.1 mmol, 10 mol % of 5 wt % Pt on carbon) in a 10 mL Hastelloy shaker tube to which liquid $NH_3$ (1.0 g, 58.7 mmol, 59 eq.) was added. The mixture was heated at 200° C. for 45 h. The mixture was cooled to ambient temperature and the excess $NH_3$ removed by $N_2$ purge. The crude mixture was suspended in 10 mL anhydrous methanol, the catalyst was removed by syringe filtration, and the crude reaction mixture was concentrated in vacuo. Glutaronitrile conversion was 97.2% to give 0.06 mmol of 2,6-diaminopyridine in 4.8% net yield.

Example 10 demonstrates the preparation of 3-methylpyridine-2,6-diamine by means of the reaction:

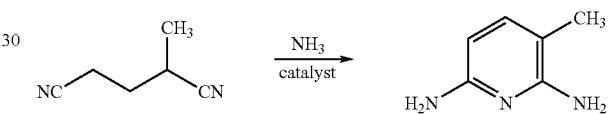

Example 10

2-Methylglutaronitrile was combined with Pd.C (5 mol % of 10 wt % Pd on carbon) in a 10 mL Hastelloy shaker autoclave to which liquid $NH_3$ was added. The mixture was heated at 200° C. for 45 h. The mixture was cooled to ambient temperature and the excess $NH_3$ removed by $N_2$ purge. The crude mixture was suspended in 10 mL anhydrous methanol, the catalyst was removed by syringe filtration, and the crude reaction mixture was concentrated in vacuo. 2-Methylglutaronitrile conversion was 100% to give 0.02 mmol of 3-methylpyridine-2,6-diamine in 2.3% net yield.

Example 11 demonstrates the preparation of a new compound by means of the reaction:

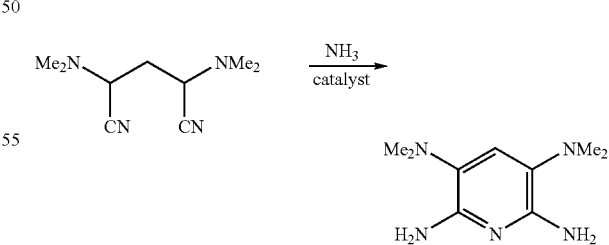

Example 11

2,4-bis(dimethylamino)pentanedinitrile (95 mg, 0.53 mmol, 1 eq.) was combined with Pd.C (56 mg, $5.3 \times 10^{-2}$ mmol, 10 mol % of 10 wt % Pd on carbon) and anhydrous $NH_3$ (1 g, 0.60 mol, 113.0 eq.) in a 10 mL Hastelloy shaker.

The crude mixture was suspended in 10 mL anhydrous methanol, the catalyst was removed by syringe filtration, and the crude reaction mixture was concentrated in vacuo. 2,4-Bis(dimethylamino) pentanedinitrile conversion was >95%. The product, $N^3,N^3,N^5,N^5$-tetramethylpyridine-2,3,5,6-tetraamine ($M^+$195), was detected by GC/MS.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than all of the features of any described embodiment, which subcombination may be characterized by the absence of the features omitted to form the subcombination; (2) each of the features, individually, included within the combination of any described embodiment; and (3) other combinations of features formed by grouping only selected features of two or more described embodiments, optionally together with other features as disclosed elsewhere herein.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

What is claimed is:

1. A process for the synthesis of a compound as described by the structure of Formula (I)

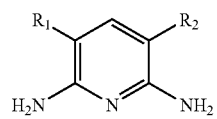

I comprising contacting a compound as described by the structure of Formula (II)

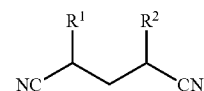

II with a chemical oxidant, and optionally also with a dehydrogenation catalyst, in liquid ammonia neat, or in a mixture of liquid ammonia and a polar, aprotic solvent, to form a reaction mixture; and heating the reaction mixture to produce a Formula (I) compound;
wherein $R^1$ and $R^2$ are each independently selected from
(a) H; (b) a hydrocarbyl group;
(c) $NR^3R^4$ wherein $R^3$ and $R^4$ are each independently selected from H and a hydrocarbyl group;

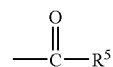

(d)

wherein $R^5$ is a hydrocarbyl group; and (e) $YR^6$ wherein Y is selected from O and S and $R^6$ is selected from H, a hydrocarbyl group, and

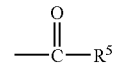

wherein $R^5$ is a hydrocarbyl group.

2. The process of claim 1 wherein one or both of $R^1$ and $R^2$ is H.

3. The process of claim 1 wherein one or both of $R^1$ and $R^2$ is $NH_2$.

4. The process of claim 1 wherein one or both of $R^1$ and $R^2$ is $N(CH_3)_2$.

5. The process of claim 1 wherein the reaction mixture comprises liquid ammonia neat.

6. The process of claim 1 wherein the reaction mixture comprises liquid ammonia and a polar, aprotic solvent.

7. The process of claim 1 wherein the reaction mixture comprises a chemical oxidant in the absence of a dehydrogenation catalyst.

8. The process of claim 1 wherein the reaction mixture comprises a chemical oxidant and a dehydrogenation catalyst.

9. The process of claim 1 wherein the reaction mixture comprises a chemical oxidant, and the chemical oxidant is selected from the group consisting of sulfur, sulfur dioxide, oxygen, selenium, 2,3-dichloro-5,6-dicyano-p-benzoquinone, 2,3,5,6-tetrachloro-p-benzoquinone, aluminum chloride, arsenic oxide, manganese dioxide, potassium ferricyanide, nitrobenzene, chlorine, bromine, and iodine.

10. The process of claim 1 wherein the reaction mixture comprises a dehydrogenation catalyst, and the dehydrogenation catalyst comprises a homogeneous catalyst.

11. The process of claim 10 wherein the homogeneous catalyst comprises at least one metal or metal salt, wherein the at least one metal or metal salt is selected from elements of Group VIII and salts of said elements.

12. The process of claim 10 wherein the homogeneous catalyst is selected from the group consisting of ruthenium, rhodium, palladium, osmium, iridium, platinum; and salts thereof.

13. The process of claim 1 wherein the reaction mixture comprises a dehydrogenation catalyst, and the dehydrogenation catalyst comprises a heterogeneous catalyst.

14. The process of claim 13 wherein the heterogeneous catalyst comprises at least one metal or metal salt and a support, wherein a metal or metal salt is selected from elements of Groups IVA, VA, VIA, VIIA, VIII, IB and IIB of the periodic table, and salts of said elements.

15. The process of claim 14 wherein the support is selected from the group consisting alumina, titania, cobaltic oxide, zirconia, ceria, molybdenum oxide, tungsten oxide, silica, silicalite, titania, a zeolite or zeotype material having a structure made up of tetrahedra joined together through oxygen atoms to produce an extended network with channels of molecular dimensions and having SiOH and/or AlOH groups on the external or internal surfaces, activated carbon, coke, and charcoal.

16. The process of claim 6 wherein the polar, aprotic solvent is selected from the group consisting of 1,4-dioxane, tetrahydrofuran, acetone, acetonitrile, dimethylformamide, pyridine, and a mixture of 1,4-dioxane plus pyridine.

17. The process of claim 1 further comprising a step of subjecting the Formula (I) compound to a reaction to prepare therefrom a compound, oligomer or polymer.

18. The process of claim 17 wherein a polymer prepared comprises a pyridobisimidazole-2,6-diyl(2,5-dihydroxy-p-phenylene) polymer, or a poly[(1,4-dihydrodiimidazo[4,5-b:4',5'-e]pyridine-2,6-diyl) (2,5-dihydroxy-1,4-phenylene)] polymer.

19. A compound as described by the structure of Formula (III):

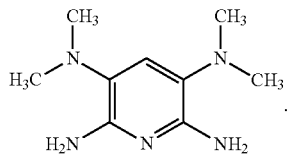

III

* * * * *